United States Patent
Xu et al.

(10) Patent No.: US 6,632,430 B2
(45) Date of Patent: Oct. 14, 2003

(54) MODULATORS OF METHYLATION FOR CONTROL OF BACTERIAL VIRULENCE

(75) Inventors: Mingxu Xu, San Diego, CA (US); Quinghong Han, San Diego, CA (US); Yuying Tan, San Diego, CA (US)

(73) Assignee: AntiCancer, Inc., San Diego, CA (US)

( * ) Notice: Subject to any disclaimer, the term of this patent is extended or adjusted under 35 U.S.C. 154(b) by 0 days.

(21) Appl. No.: 10/334,532

(22) Filed: Dec. 30, 2002

(65) Prior Publication Data

US 2003/0138414 A1 Jul. 24, 2003

Related U.S. Application Data

(62) Division of application No. 09/591,078, filed on Jun. 9, 2000, now abandoned.
(60) Provisional application No. 60/138,307, filed on Jun. 9, 1999.

(51) Int. Cl.[7] .......................... A61K 38/51; C12N 9/00; C12N 9/88
(52) U.S. Cl. .................... 424/94.5; 435/183; 435/232
(58) Field of Search ................... 435/183, 232; 424/94.5

(56) References Cited

U.S. PATENT DOCUMENTS

| 4,381,004 A | 4/1983 | Babb |
| 4,507,287 A | 3/1985 | Dixon |
| 5,872,104 A | 2/1999 | Vermeulen et al. |
| 6,001,840 A | 12/1999 | Montgomery et al. |

FOREIGN PATENT DOCUMENTS

| EP | 0 334 361 A | 9/1989 |
| EP | 0 347 852 A | 12/1989 |
| EP | 0 365 849 A | 5/1990 |
| JP | 54055727 | 5/1979 |
| JP | 354135222 | 10/1979 |
| WO | WO 96 20010 A | 7/1996 |

OTHER PUBLICATIONS

Braaten, B.A. et al. (1994) *Cell* 76:577–588.
Heithoff, D.M. et al. (1999) *Science* 284:967–970.
Liu, S. et al. (1992) *Antiviral Research* 19:247–265.
Minatto, et al. (1998) *Exp Parasitology*: 175–180.

Primary Examiner—Michael Meller
(74) Attorney, Agent, or Firm—Morrison & Foerster LLP

(57) ABSTRACT

Compositions and methods which ameliorate the virulence of bacterial infection are described wherein the active ingredient modulates transmethylation reactions in bacterial cells. Particularly useful compounds are inhibitors of S-adenosyl methionine synthetase (SAMS), of S-adenosyl homocysteine hydrolase (SAHH) and of transmethylases.

13 Claims, No Drawings

MODULATORS OF METHYLATION FOR CONTROL OF BACTERIAL VIRULENCE

This application is a divisional of U.S. Ser. No. 09/591,078 filed Jun. 9, 2000 abandoned which application claims priority from Ser. No. 60/138,307 filed Jun. 9, 1999. The contents of these applications are incorporated herein by reference.

TECHNICAL FIELD

The invention relates to the control of bacterial infection in animals. More particularly, it relates to the use of inhibitors of bacterial transmethylation pathways to control such infection.

BACKGROUND ART

The importance of transmethylation reactions in metabolism in general has gained considerable recognition. PCT application WO96/20010 and U.S. Pat. No. 5,872,104, incorporated herein by reference, describe the use of methylation inhibitors to reduce the resistance of microorganisms to antibiotics. Heithoff, D. M., et al,. *Science* (1999) 284:967–970 report the results of a study showing that *Salmonella typhimurium* which lacks DNA adenine methylase (Dam) were essentially avirulent and therefore could be used as live vaccines against murine typhoid fever. The authors concluded that Dam regulated the expression of at least 20 genes known to be induced during infection and noted that inhibitors of Dam were likely to be antimicrobials. It was earlier shown by Braaten, B. A., et al,. *Cell* (1994) 76:577–588 that the methylation patterns associated with pyelonephritis-associated pili (Pap) DNA controlled gene expression in *E. coli*. Thus, it is clear that in bacteria, methylation status is significant in controlling metabolism, and thus infectivity in general. The importance of S-adenosyl-L-methionine (SAM) dependent transmethylation in viral infection has also been studied by Liu, S., et al., *Antiviral Research* (1992) 19:247–265.

S-adenosyl-homocysteine hydrolase (SAHH) is significantly related to transmethylation by virtue of its ability to regulate the ratio of SAM to S-adenosylhomocysteine (SAH). SAHH catalyzes the equilibrium between SAH and its lysis products, adenosine and homocysteine. It is significant in regulating the levels of adenosine as well. SAHH has been used as a target for antiparasitic and antiviral chemotherapy as described by Minatto, et al,. *Experimental Parasitol* (1998) 175–180. SAM is the source of methyl groups for all transmethylation reactions and SAH constitutes a methylation inhibitor. Thus, if SAHH which controls the ratio of SAM to SAH is inhibited, this will result in modulating the transmethylation metabolism of the bacterium, and consequently, the virulence of the bacterium. Methylation processes are also affected by methionine levels, and agents that deplete methionine, such as methionine-α,γ-lyase (methioninase) are effective to modulate methylation status as well.

Although it seems generally understood that methylation status and control of transmethylation is significant in the metabolism and life cycle of bacterial cells, and although means to modulate methylation status and transmethylation are known in the art, surprisingly, such means have not been used to control or otherwise ameliorate bacterial infection. The present invention is directed to taking advantage of the significance of methylation in designing antibiotic protocols.

DISCLOSURE OF THE INVENTION

The invention provides methods and compositions for the amelioration of bacterial virulence by modulating the transesterification systems of the bacteria through control of cellular components that catalyze the relevant reactions or by depleting the reservoir of available methyl groups. In addition, the invention provides means to assess the potency of antivirulent compound candidates by assaying their effects on these cellular components.

In one preferred aspect, the invention is directed to a method to diminish bacterial virulence by supplying agents which inhibit enzymes that affect methylation such as transmethylases, S-adenosyl methionine synthetase (SAMS), S-adenosyl-homocysteine hydroxylase (SAHH), or DNA adenine methylase (Dam). Such inhibitors comprise adenosine analogs and homocysteine analogs.

In another preferred aspect, the invention is directed to methods to identify successful antivirulent agents by assessing their ability to inhibit enzymes involved in methylation, such as transmethylases, SAHH or Dam.

In still another aspect, the invention is directed to a method of treating virulent bacterial infection by administering a composition comprising methioninase, or an expression system therefor.

MODES OF CARRYING OUT THE INVENTION

The present invention is based on the recognition that transmethylation reactions and methylation levels are significant in controlling bacterial infectivity, proliferation and growth. Although this recognition exists in the art, no advantage has been taken of this recognition to provide antibiotic protocols for prophylactic or therapeutic treatment of bacterial infection. The present invention remedies this by providing not only therapeutic protocols and compositions useful in combating bacterial infection, but also in providing means to identify new agents as antibiotics by virtue of their ability to interfere with methylation traffic in bacteria.

The invention's contribution is particularly important in view of the ability of bacteria to acquire resistance to antibiotics as these compounds become more universally employed. By basing antibiotic treatment on metabolic functions which have not so far been targeted, the possibility of acquisition of resistance as a simple modification of resistance pathways already acquired is minimized.

In general, any agent which interferes with the methylation pathways critical to virulence, infectivity, or growth and proliferation may be targeted. Some appropriate targets include the enzymes which catalyze the transmethylation reactions per se, such as Dam, enzymes which regulate the levels of methyl donors, such as SAHH, and enzymes which directly regulate the supply of methyl groups such as methioninase. Thus, it would be desirable in most cases to inhibit those enzymes that mediate transmethylation, although by encouraging methylation reactions that are undesirable, enhancement of activity may be helpful. It is also most useful to inhibit enzymes which indirectly affect the methylation reactions, such as SAHH, which inhibition causes the levels of SAH to increase, which in turn enhances the ability of S-adenosyl-L-methionine (SAM) to effect methylation reactions. Enzymes that deplete the supply of viable methyl groups such as methionine-α,γ-lyase (methioninase) are typically stimulated or the levels of these enzymes enhanced. The choice of antimicrobial agent will depend on the selected targets.

Agents that generally inhibit methylation include those set forth in U.S. Pat. No. 5,872,104, the contents of which are incorporated herein by reference. The disclosure of this document recognizes the utility of methylation inhibitors in controlling infection, but only in the context of treatment with a second, established antibiotic wherein the methylation inhibitor is designed to mitigate the resistance the bacterium may have mounted against the co-administered antibiotic. As is recognized in the '104 patent, a multiplicity of agents that inhibit RNA methyltransferase enzymes is exemplified by SAH itself and its analogs, homocysteine, adenine derivatives, and SAM analogs and derivatives such as 6-amino-1-hexylnitrogen analogs of SAM. Other inhibitors of RNA methyltransferases are also disclosed. Agents that inhibit SAHH are also recognized, such as adenosine dialdehyde and 3-deaza adenosine, as well as structural analogs of SAH.

The '104 patent also notes that SAM synthetase inhibitors will be useful, including, for example, L-cis-AMB and L-cis-AMTB. It is further noted that agents that inhibit the synthesis of glutathione also inhibit SAM synthetase.

In addition, transmethylase inhibitors include DHFR inhibitors such as methotrexate, and compounds that inhibit polyamine synthesis and the like are also noted.

In one preferred aspect, the invention comprises compositions and methods for diminishing the virulence of bacterial infection which use as an active ingredient at least one inhibitor of SAHH. While not intending to be bound by any theory, it is believed that inhibitors of SAHH interfere with methylation by causing the concentration of SAH to build up; SAH is a methylation inhibitor. A wide variety of such inhibitors is known. For example, suicide inactivation of human lymphoblast SAHH by 2'-deoxyadenosine and adenine arabinoside has been reported by Hershfield, M. S., *J Biol Chem* (1979) 254:22–25. The ability of 6'-(E and Z)-halohomovinyl derivatives of adenosine to inhibit SAHH was reported by Wnuk, S., et al., *J Med Chem* (1994) 37:3579–3587. Another such inhibitor is S-(1,2-dichlorovinyl)-L-homocysteine (DCVHC), Lash, L. H., et al., *Arch Biochem Biophys* (1986) 251:432–439. In addition, a variety of inhibitors of SAM-dependent methyltransferases in general which are analogs of S-aristeromycinyl-L-homocysteine are disclosed by Houston, D. M., et al., *J Med Chem* (1985) 28:478–482. All of these documents are incorporated herein by reference.

As set forth above, other preferred targets are Dam, SAMS, and the like. Suitable inhibitors for these enzymes are also known in the art.

In still another preferred embodiment, the levels of activity of the methioninase are enhanced. Use of methioninase in treating cancer and other hyperproliferative conditions is disclosed in PCT publications WO94/11535 and WO96/40284. Treatment of tumors by gene therapy involving the expression of the methioninase coding sequence is described in U.S. Ser. No. 09/195,055 filed Nov. 18, 1998 and incorporated herein by reference. The invention thus also relates to depleting the source of methyl groups by supplying methioninase to deplete the levels of methionine. The use of methioninase to effect such depletion in order to treat malignant diseases has been disclosed in U.S. Pat. No. 5,690,929 incorporated herein by reference. The methods of administration and formulation therein described are equally applicable here.

The compositions of the invention may comprise as active ingredients one or more specific inhibitors of SAHH or inhibitors of SAM-dependent transmethylases in general. Many of these inhibitors are adenosine analogs as is understood in the abovecited art; however other suitable inhibitors are numerous and known in the art.

The antivirulence compounds regulating methylation levels and status can be administered to suitable subjects either as the sole active ingredient, or several such compounds may be used in combination, or these may be used in combination with additional antimicrobial agents. However, unlike the case with the description of U.S. Pat. No. 5,872,104, co-administration with traditional antibiotics is not required. The nature of the formulation and mode of administration will depend on the nature of the subject, the nature of the bacterial infection, the severity of the infection, and a variety of other factors well known to medical and veterinary practitioners. Suitable subjects include, in addition to humans, domestic animals and avians, livestock intended for commercial purposes, experimental animals for use in research, and the like. Depending on the parameters cited above, the mode of administration may be systemic or topical or local. Systemic administration may be by injection or by transdermal, transmucosal, or oral administration. Suitable formulations for any appropriate mode of administration may be found, for example, in *Remington's Pharmaceutical Sciences*, latest edition, Mack Publishing Co., Easton, Pa. The methylation modulating virulence inhibitors within the scope of the invention, with the exception of proteins such as methioninase, are typically small molecules that are readily subject to conventional formulation and administration techniques.

Thus, the compounds used for the antibiotics may be administered orally in the form of capsules, pills, or powders or may be contained in syrup. They may also be administered intranasally using formulations which include surfactants in order to penetrate nasal barriers; by suppository, by transdermal patch, by injection, either intravenously or by subcutaneous or intramuscular or intraperitoneal injection. Compositions suitable for intravenous injection typically may include, in addition to isotonic carrier media, liposomal formulations of the active ingredient. For localized treatment, such as infection of the eyes, the agents may be administered in the form of eye drops; for infections localized at wound sites, local administration topically is also preferred.

With respect to the administration of compounds other than small molecules, such as methioninase, more specialized techniques are required as proteins are difficult to administer systemically. However, such proteins can be injected, typically intravenously and by proper formulation other routes of administration may be also used. Intranasal administration has been frequently successful. A variety of means for administration is available in the art generally. In addition, the protein may be supplied by providing a suitable expression system either using simply naked DNA or including in the DNA administered a means to effect integration of the DNA into the genetic material of a cell which may be modified ex vivo and readministered. Alternatively, viral vectors, such as adenovirus, retrovirus and the like may be directly employed. The techniques for such "genetic therapy" are currently under development and the techniques themselves do not constitute part of the invention. That is to say that the insight provided by the inventors herein is that enhanced levels of methioninase are helpful in combating bacterial infection, however these enhanced levels are achieved.

In an additional aspect, the invention provides means to identify compounds useful in ameliorating bacterial infection virulence. Isolated forms of transmethylation enzymes, such as DNA adenosine methylase (Dam) or of enzymes that modulate methylation in general, such as SAHH, may be used. By "isolated" form is meant that the enzyme is present in the assay in a context in which it is not natively found. The isolated enzymes may also, preferably, be purified for ease of interpretation of the assay results. Means to assay the activity of these enzymes are conventional and involve supplying substrates which cause detectable label either to increase or decrease as they are converted to product by the relevant enzyme. In general, compounds which inhibit these enzymes will be useful to ameliorate bacterial virulence.

A wide variety of assay techniques to determine the ability of a compound being tested to inhibit a particular enzyme is available in the art. For example, potential inhibitors of SAHH may be added as test compounds to reaction mixtures which contain the isolated enzyme, SAH (the substrate) and a homocysteinase. The homocysteine produced by the action of SAH hydrolase on SAH can then be detected by measuring, for example, the hydrogen sulfide, ammonia, or x-ketoglutarate produced by the lysis of homocysteine. Such assay techniques are described, for example, in U.S. Pat. No. 6,066,467 and PCT application US98/15430, both incorporated herein by reference. A wide variety of assay systems which employ SAHH, Dam and other enzymes which modulate methylation is available in the art.

The purified form of the relevant enzymes can be obtained by extraction from their natural source, recombinant synthesis, or, in some cases, by chemical synthesis from the individual amino acid constituents.

What is claimed is:

1. A method for treating a bacterial infection which method comprises administering to a subject in need thereof an amount of methioninase sufficient to treat such infection.

2. A method for treating a bacterial infection which method comprises identifying a subject afflicted with bacterial infection and administering to said subject in need thereof an effective amount of methioninase sufficient to treat such infection.

3. The method of claim 2 wherein the subject is human.

4. The method of claim 2 wherein the subject is a domestic animal or avian.

5. The method of claim 2 wherein the subject is livestock.

6. The method of claim 2 wherein the subject is an experimental animal intended for use in research.

7. The method of claim 2 wherein said administering is intravenous or intranasal.

8. A method for treating a bacterial infection which method comprises identifying a subject afflicted with bacterial infection and treating said subject wherein said treating consists of administering to said subject in need thereof an effective amount of methioninase sufficient to treat such infection.

9. The method of claim 8 wherein the subject is human.

10. The method of claim 8 wherein the subject is a domestic animal or avian.

11. The method of claim 8 wherein the subject is livestock.

12. The method of claim 8 wherein the subject is an experimental animal intended for use in research.

13. The method of claim 8 wherein said administering is intravenous or intranasal.

* * * * *